United States Patent
Schubert et al.

(10) Patent No.: US 7,442,181 B2
(45) Date of Patent: Oct. 28, 2008

(54) DEVICE FOR DISPENSING MEDICAL ACTIVE INGREDIENTS

(75) Inventors: Ernst-Wilhelm Schubert, Lübeck (DE); Götz Kullik, Lübeck (DE); Tilman von Blumenthal, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 719 days.

(21) Appl. No.: 10/738,463

(22) Filed: Dec. 17, 2003

(65) Prior Publication Data

US 2004/0171985 A1 Sep. 2, 2004

(30) Foreign Application Priority Data

Feb. 27, 2003 (DE) ................. 103 08 401

(51) Int. Cl.
*A61M 5/30* (2006.01)
(52) U.S. Cl. .................................. 604/65
(58) Field of Classification Search ............. 604/82–91, 604/93.01, 264, 257, 247, 250, 256, 65–67; 427/2.1; 424/423
See application file for complete search history.

(56) References Cited

U.S. PATENT DOCUMENTS

| | | | |
|---|---|---|---|
| 4,756,706 A * | 7/1988 | Kerns et al. ................ 604/66 |
| 4,915,688 A * | 4/1990 | Bischof et al. ............. 604/83 |
| 5,531,697 A | 7/1996 | Olsen et al. |
| 5,531,698 A | 7/1996 | Olsen |
| 5,873,731 A * | 2/1999 | Prendergast ............... 434/262 |
| 6,077,055 A * | 6/2000 | Vilks ......................... 417/478 |
| 6,491,666 B1* | 12/2002 | Santini et al. ............. 604/191 |
| 7,150,724 B2* | 12/2006 | Morris et al. ............. 604/131 |
| 2003/0088238 A1 | 5/2003 | Poulsen et al. |
| 2006/0122577 A1 | 6/2006 | Poulsen et al. |

FOREIGN PATENT DOCUMENTS

| DE | 299 22 736 | 6/2001 |
|---|---|---|
| WO | WO 95/28190 | 10/1995 |
| WO | WO 03/026726 A1 | 4/2003 |

* cited by examiner

*Primary Examiner*—Nicholas D. Lucchesi
*Assistant Examiner*—Christopher D Koharski
(74) *Attorney, Agent, or Firm*—McGlew & Tuttle, P.C.

(57) ABSTRACT

A device and system for dispensing medical active ingredients. Medical active ingredients may be, e.g., drugs or anesthetics, which enter the patient's bloodstream. Injection pumps and perfusors are usually used for their dispensing, and vapors are frequently used in the case of inhalation anesthetics. The device permits the dispensing of a plurality of medical active ingredients, in which the rates of dispensing can be set precisely and changed with rapid action. This is accomplished by the series connection of a plurality of devices according to the present invention, which are designed as modules. Each module comprises a cartridge (6) as well as a delivery device (8) for delivering the particular medical active ingredient to be administered to a fluid interface (18), which leads to a supply line (16) designed either as an infusion line or as a respiration tube. The module has a coupling means (9, 10, 11, 12).

13 Claims, 1 Drawing Sheet

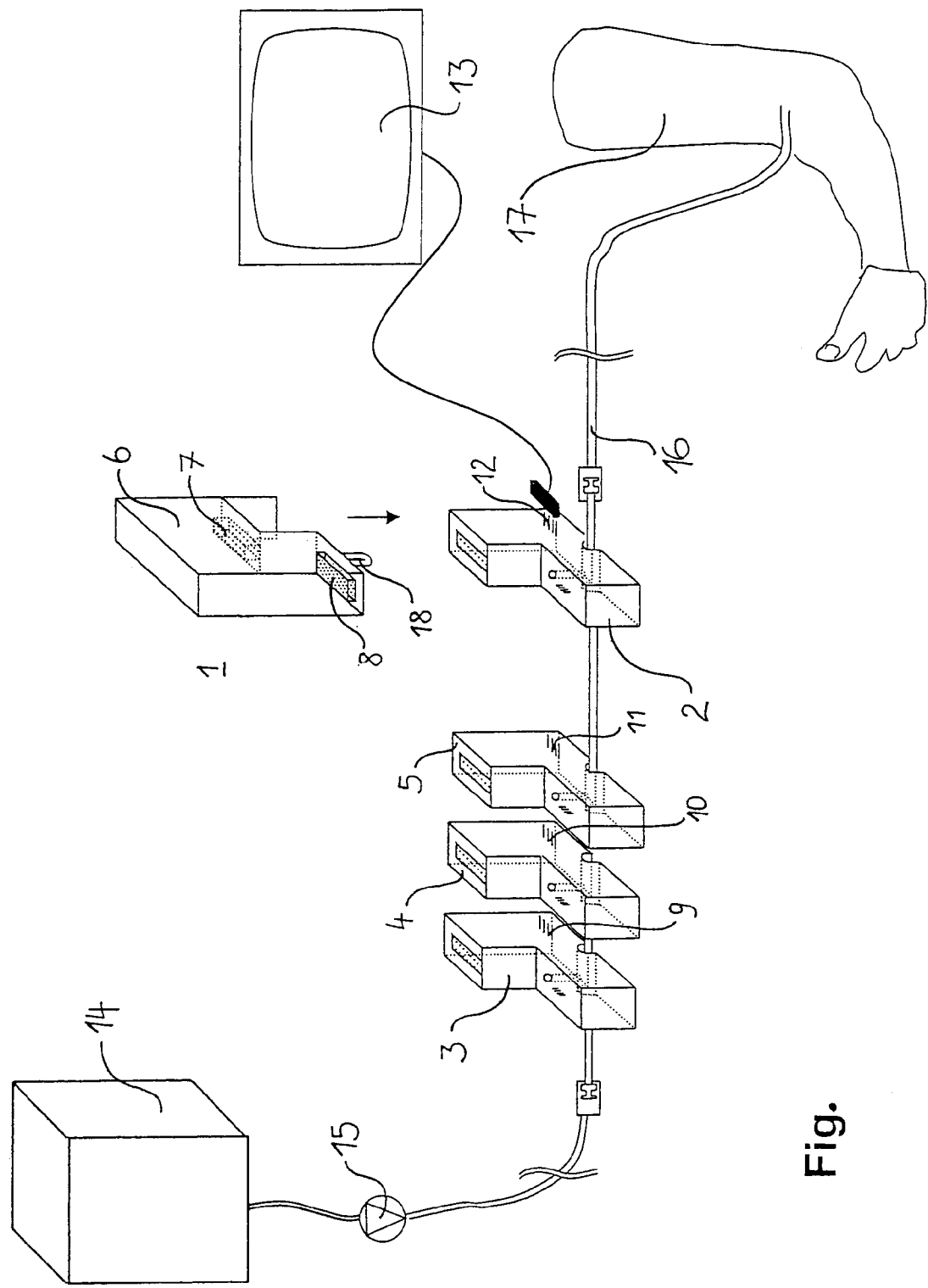
Fig.

DEVICE FOR DISPENSING MEDICAL ACTIVE INGREDIENTS

FIELD OF THE INVENTION

The present invention pertains to a device and system for dispensing medical active ingredients and more particularly to devices in which the liquid medical active ingredients are fed to the patient at an exactly defined rate.

BACKGROUND OF THE INVENTION

Injection pumps and perfusors are used for the controlled dispensing of medical active ingredients, which may be, e.g., drugs or anesthetics that enter the patient's bloodstream. Vapors are frequently used in the case of anesthetics that enter the patients respiration circulation, the so-called inhalation anesthetics. In the case of perfusors, the liquid medical active ingredients are pushed forward by the piston of a syringe at an exactly defined rate. The rates of delivery are approximately 0.5 mL to 20 mL per hour. While no mixtures, but at most an individual anesthetic is administered in the case of anesthetics, the dispensing of 10 or more different drugs for one patient is not a rarity. Additional drugs are sometimes also added during a therapy. Every individual drug is diluted differently with a carrier liquid, e.g., a Ringer's solution. In light of technical defects, the pressure and the output of the pump is usually monitored. Based on the compliance of the tubes, errors caused by other factors, e.g., reduced rates of dispensing, which may be caused by stenosis in the patient, are detected only with a certain time delay.

If the rate of dispensing is changed for a medical active ingredient, the time period until effectiveness appears in the patient cannot be precisely determined because of the compliance of the entire system, because if different drugs are dispensed by means of injection pumps and integrated in a bank of stopcocks, the time period until an individual drug becomes effective is additionally determined by the overall volume flow from all injection pumps between the bank of stopcocks and the patient's bloodstream. The medical active ingredient and the carrier solution are usually drawn up manually in the syringes for the injection pumps and perfusors, labeled and introduced. A rate of dispensing is subsequently set. It is obvious that human error may become a cause for a nonoptimally adapted medication in such a situation.

The infusion device with central control device and a plurality of infusion apparatus for liquid medical active ingredients, which better meets the safety requirements according to the above explanations, is known from Utility Model No. DE 299 22 736 U1. In the case of the infusion device, each infusion apparatus has an unmistakable code number, which is sent to a control device, which will then send corresponding signals to the infusion apparatus. Precautions are thus taken against an error in dispensing. However, the problem of accurately determining and changing the rates of dispensing still remains to be solved.

SUMMARY OF THE INVENTION

It is an object of the present invention to provide a device for dispensing a plurality of medical active ingredients, with which the rates of dispensing can be set accurately and changed with rapid action.

According to the invention, a device is designed as a module with coupling means and a fluid interface. The mechanical coupling means of the module may additionally contain electric and data couplings. Using the coupling means, it is possible to connect a plurality of modules in series. The fluid interfaces of the module may be connected to a supply line to a patient. Individual modules are added or removed as desired, without having to interrupt the supply line or to design it differently. The module comprises a cartridge for accommodating a medical active ingredient. This may be, e.g., a drug to be administered in the liquid form through the patient's bloodstream or an anesthetic. The anesthetic that is considered for use is, in principle, an anesthetic administered by infusion or by inhalation. In the first case, the module has a fluid interface to a supply line that is designed as an infusion line and leads to the patient, and a fluid interface designed differently from the former is necessary in the second case, because the connection to a supply line designed as a respiration tube is established. A fluid interface means in both cases that the interface establishes the connection to a supply line that carries a flowing medium, namely, a fluid, i.e., either a liquid or a gas, in its interior. The module comprises, furthermore, a delivery means for delivering the medical active ingredient from the cartridge to the fluid interface and finally into the supply line leading to the patient.

In an advantageous embodiment, the cartridge of the module comprises an upper part, which accommodates the cartridge for the medical active ingredient, the delivery means and the fluid interface, and a lower part, which is designed as a holder for the upper part and comprises the coupling means.

The delivery means is preferably designed as a micropump. Such a pump has an individual dispensing volume that is approximately between 0.2 µL and 3 µL and a maximum pumping frequency in the range of 30 Hz to 200 Hz. This results in a maximum rate of delivery that is approximately between 0.36 mL and 36 mL per minute. The small individual dispensing volume permits the accurate dispensing of very small quantities of a medical active ingredient, so that it is also possible to administer, e.g., drugs in a more highly concentrated solution.

In another preferred embodiment of the present invention, the cartridge has a code. Machine-readable information on the medical active ingredient that is contained in the cartridge is thus stored. The information pertains, e.g., to the ingredients, the active ingredient concentrations, the date of manufacture and the expiration date, an identification number as well as the manufacturer. This information is stored, e.g., electronically, magnetically or as a bar code.

In another advantageous embodiment of the cartridge, the cartridge is designed as a disposable article that can be detached from the module and disposed of after use. As an alternative, it would be conceivable to have the cartridge refilled by the manufacturer or a pharmacy after its use.

It may also be advantageous to manufacture the entire module as a disposable article. It is ensured by the single-time use that the module is free from microorganisms, which is especially significant for supply lines that are designed as infusion lines and not as respiration tubes, i.e., lead directly into the patient's bloodstream.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The FIGURE shows a module according to the present invention for dispensing a medical active ingredient.

DESCRIPTION OF THE PREFERRED EMBODIMENT

Referring to the drawings in particular, the Figure shows a module according to the present invention for dispensing a medical active ingredient, which comprises an upper part 1 and a lower part 2. Only the lower parts 3, 4, 5 of three other modules for dispensing different medical active ingredients are shown. The lower parts have the same design as the lower part 2. The lower part 2 is designed as a holder and is used to accommodate the upper part 1, which has a cartridge 6 with a code 7 as well as a delivery means 8 designed as a micropump. The upper part 1 is plugged onto the lower part 2 vertically downwardly in the direction of the arrow. The lower parts 3, 4, 5 as well as the lower part 2 may be connected in series, and they can be connected via coupling means 9, 10, 11. Each lower part 3, 4, 5 has a coupling means with a first coupling part (or first side coupler part) 9, 10, 11 each on its side facing the viewer. On its side facing the viewer, the lower part 2 also has the coupling means with a first coupling part (or first side coupler part) 12, which establishes the connection of the series-connected modules to an evaluating and control unit 13. This coupling means with coupling parts 9, 10, 11, 12, which provides an electric and data coupling, besides the mechanical connection. For example, the information stored on the code 7 is transmitted to the evaluating and control unit 13 and processed there. Each coupling means also includes a receiving part or second side coupler part of each lower part 2, 3, 4, 5, which optionally receives the coupling parts 9, 10, 11 of the respective adjacent module. The receiving part is located at the lower part 2 as well as at the lower parts 3, 4, 5 on the side that is not visible to the viewer of the Figure, but is shown in phantom line. The cartridge 6 located in the upper part 1 is used to receive a medical active ingredient to be administered. All medical active ingredients are fed here in the manner of a so-called umbilical cord infusion. A carrier liquid, e.g., Ringer's solution, is sent here from a container 14 to the arm of a patient 17 by means of a conventional pump 15 via a supply line 16. The medical active ingredient reaches the fluid interface 18 and the supply line 16 from the cartridge 6 through the delivery means 8 at a rate of dispensing set in advance. The fluid interface 18 is designed as a hollow needle.

While a specific embodiment of the invention has been shown and desribed in detail to illustrate the application of the invention, it will be understood that the invention may be imbodied otherwise without departing from such principles.

What is claimed is:

1. A medical active ingredient dispensing system, comprising:
    a carrier liquid container;
    a supply line leading from said carrier liquid container to a patient;
    a module with a base part having a coupler including a first side coupler part and a second side coupler part for receiving and sending electricity and data for series connection with a base part having a coupler of another adjacent module, and a cartridge with a fluid interface for connection to the supply line leading to the patient, said cartridge for receiving and holding a medical active ingredient and including a delivery device for delivering the medical active ingredient from said cartridge to said fluid interface and into said carrier liquid in said supply line, said base part having a cartridge holding means for accommodating said cartridge and positioning said fluid interface relative to said base and relative to the supply line;
    another module with a base part having a coupler including a first side coupler part and a second side coupler part for receiving and sending electricity and data for series connection with a base part having a coupler of another adjacent module, and a cartridge with a fluid interface for connection to the supply line leading to the patient, said cartridge for receiving and holding a medical active ingredient and including a delivery device for delivering the medical active ingredient from said cartridge to said fluid interface and into said carrier liquid in said supply line, said base part of said another module having a cartridge holding means for accommodating said cartridge of said another module and positioning said fluid interface of said another module relative to said base of said another module and relative to the supply line, said module and said another module being coupled in series with one of said first side coupler part and second side coupler part of said module coupled with one of said first side coupler part and second side coupler part of said another module and with each of said module fluid interface and said another module fluid interface connected to said supply line; and
    an evaluating and control unit for processing data from connected modules and for receiving stored information, said evaluation and control unit being connected to each of said module and said another module via one of said first side coupler part of said module, said second side coupler part of said module, said first side coupler part of said another module and said second side coupler part of said another module.

2. A system in accordance with claim 1, wherein said delivery device comprises a micropump.

3. A system in accordance with claim 1, wherein said cartridge has a code means for passing medical active ingredient information from said cartridge to said lower part.

4. A system in accordance with claim 3, wherein said delivery device receives delivery information associated with said medical active ingredient information with said delivery information being provided by a code reader for reading said code of said cartridge.

5. A system in accordance with claim 4, wherein said coupler includes pins and a receiving portion for coupling with pins of an adjacent module for electric and data coupling and mechanical connection.

6. A system in accordance with claim 5, Wherein said stored information received said evaluating and control unit includes information stored on the code.

7. A system in accordance with claim 1, wherein said cartridge comprises a disposable article detachably connected to said base part of said module.

8. A medical active ingredient dispensing system, comprising:
    a solution container;
    a pump;
    a supply line leading from said solution container to a patient connection location, said pump for feeding solution from said container to said patient connection location;
    a first module base part comprising:
        a first module supply line receiving portion, said first supply line extending through said first module supply line receiving portion;

a first module cartridge holding means for cartridge accommodation and for fluid interface positioning relative to said first module base and relative to said supply line; and a first module coupler including a first module first side coupler part for receiving and sending electricity and a first module second side coupler part for receiving and sending electricity;

a first module cartridge with a shape for connecting to said first module base part via said first module cartridge holding means to position said first module cartridge relative to said first module base part, said first module cartridge defining a first medical active ingredient container with medical active ingredient therein and said first module cartridge comprising;

a first module fluid interface for connecting to the supply line at said first module supply line receiving portion and a first module delivery device delivering the medical active ingredient from said cartridge through said fluid interface to said supply line;

a second module base part comprising:

a second module supply line receiving portion, said second supply line extending through said second module supply line receiving portion;

a second module cartridge holding means for cartridge accommodation and for fluid interface positioning relative to said second module base and relative to said supply line; and a second module coupler including a second module first coupler part for receiving and sending electricity and a second module second side coupler part for receiving and sending electricity; and a second module cartridge with a shape for connecting to said second module base part via said second module cartridge holding means to position said second module cartridge relative to said second module base part, said second module cartridge defining a second medical active ingredient container with medical active ingredient therein and said second module cartridge comprising:

a second module fluid interface for connecting to the supply line at said second module supply line receiving portion; and a second module delivery device delivering the medical active ingredient from said cartridge through said fluid interface to said supply line, wherein said first module coupler is connected to said second module coupler with one of said first module first side coupler part and said first module second side coupler part connected to one of said second module first side coupler part and said second module second side coupler part with each of said first module fluid interface and said second module fluid interface connected to said supply line.

9. A system in accordance with claim 8, further comprising:

a first code means with a code element on said first cartridge and a code interface at said first base part for passing medical active ingredient information, relating to the medical active ingredient in said first cartridge, from said first cartridge to said first base part;

a second code means with a code element on said second cartridge and a code interface at said second base part for passing medical active ingredient information, relating to the medical active ingredient in said second cartridge, from said second cartridge to said second base part; and an evaluating and control unit for processing data from said first module and said second module and for receiving information stored on said first code means and said second code means and for controlling each of said first module delivery device and said second module delivery device, said evaluating and control unit being connected to said first base part and said second base part via one of said first module coupler and said second module coupler.

10. A system in accordance with claim 9, wherein each said delivery device comprises a micropump.

11. A system in accordance with claim 9, wherein each said cartridge comprises a disposable article detachably from each respective base part.

12. A system in accordance with claim 9, wherein said first module first side coupler part comprises pins and said first module second side coupler part comprises a receiving portion for coupling with pins and said second module first side coupler part comprises pins and said second module second side coupler part comprises a receiving portion for coupling with pins whereby a mechanical connection is provided by one of said first module first side coupler part and said first module second side coupler part being connected to one of said second module first coupler part and said second module second side coupler part.

13. A system in accordance with claim 9, wherein each said base unit includes a guiding structure for positioning each fluid interface relative to said supply line with a cartridge connected to a respective said base unit.

* * * * *